United States Patent [19]
Karami et al.

[11] Patent Number: 4,461,621
[45] Date of Patent: Jul. 24, 1984

[54] DISPOSABLE DIAPER WITH POLYMER COATING

[75] Inventors: Hamzeh Karami, Embourg; André Crutzen, Liége, both of Belgium

[73] Assignee: Colgate-Palmolive Company, New York, N.Y.

[21] Appl. No.: 455,188

[22] Filed: Jan. 3, 1983

Related U.S. Application Data

[63] Continuation-in-part of Ser. No. 313,040, Oct. 19, 1981.

[51] Int. Cl.³ .................. A41B 13/02; A61F 13/16
[52] U.S. Cl. .................................. 604/368; 428/286
[58] Field of Search ............... 428/286; 604/379, 380, 604/378, 368

[56] References Cited

U.S. PATENT DOCUMENTS

| | | | |
|---|---|---|---|
| 2,952,260 | 9/1960 | Burgeni | 604/374 |
| 3,078,849 | 2/1963 | Morse | 604/368 |
| 3,371,667 | 3/1968 | Morse | 604/369 |
| 3,494,362 | 2/1970 | Burgeni | 604/374 |
| 3,686,024 | 8/1972 | Nankee et al. | 428/286 |
| 3,858,585 | 1/1975 | Chatterjee | 604/376 |
| 3,860,003 | 1/1975 | Buell | 604/385 |
| 3,875,943 | 4/1975 | Fischer | 604/359 |
| 3,916,900 | 11/1975 | Breyer et al. | 604/365 |

Primary Examiner—Marion McCamish
Assistant Examiner—Nancy A. B. Swisher
Attorney, Agent, or Firm—Norman Blumenkopf; Herbert S. Sylvester; Murray M. Grill

[57] ABSTRACT

An absorbent article comprising a backing sheet of fluid impervious material, a fluid pervious cover sheet, and a first pad adjacent the cover sheet comprising a loosely formed fibrous mass. A separate second pad may be positioned intermediate the first pad and the backing sheet, with the second pad comprising a mass of fibers having compressed regions extending throughout a substantial part of the second pad. A polymer coating in the target area extends at least most of the width of the pads and extends between the third and the sixth tenth of the length of the pads. The polymer may be present on the top surface of the first pad (i.e. surface adjacent cover (top) sheet) and/or between the first and second pad and/or on the bottom or back surface of the second pad. Where only one pad is used, the polymer may be present on both the top and bottom surfaces thereof. When the polymer coating is on the top surface of the first pad and/or between the first and second pads, it is preferred that the coating be in the form of a plurality of spaced strips or bands horizontally or vertically disposed relative to the diaper length. The average interfiber spacings in the second pad are substantially less than the average interfiber spacings in the first pad such that the second pad rapidly transmits body fluids to remote locations of the second pad for retention in the areas at a location spaced from the cover sheet.

3 Claims, 6 Drawing Figures

DISPOSABLE DIAPER WITH POLYMER COATING

REFERENCE TO RELATED APPLICATION

This application is a continuation-in-part of application Ser. No. 313,040, filed Oct. 19, 1981.

BACKGROUND OF THE INVENTION

The present invention relates to disposable absorbent articles, such as diapers and the like.

A varied assortment of disposable absorbent articles have been proposed for use in receiving and retaining body fluids. Such articles, e.g., disposable diapers, sanitary napkins and the like, have normally been constructed with a fluid impervious backing sheet, a fluid pervious cover or top sheet, an absorbent pad intermediate the backing and cover sheets, such as comminuted wood pulp termed in the art as "fluff." Although increasingly popular due to disposability, certain problems remain associated with the absorbent pads which prevent the articles from being totally satisfactory.

First, it is necessary that the pads rapidly spread body fluids from the point of application toward remote locations of the pad in order to minimize pad saturation in localized areas and make maximum use of the full pad capacity. Second, it is desirable that the pad preferentially retains the body fluids at locations spaced from the cover sheet in order to minimize back wetting through the cover sheet with attendant discomfort to the wearer. Third, the pad should be soft and conformable to the shape of the wearer in order to provide a proper fit of the article and maximum comfort. Finally, the pad should be made in accordance with simplified manufacturing techniques in order to reduce the cost of the disposable article to the consumer.

It has been found that coatings of absorbent materials on the pad enhance the total amount of fluid capable of absorption by the absorbent article. These materials are the well-known suberabsorbing polymers of the acrylic type, such as the cross-linked poly aerylonitrile and the starch grafted poly acrylonitrile, as well as such products as described in U.S. Pat. Nos. 3,645,836, 3,932,322, 4,055,180, 4,055,184, 4,084,591, 4,090,013 and 4,333,461.

In my earlier filed application, Ser. No. 313,040, filed Oct. 19, 1981, there is disclosed a disposable absorbent article having a fluid impervious backing sheet and a fluid pervious top sheet, a pad assembly comprised of a loosely formed pad adjacent the cover sheet and a second pad between the first pad and the backing sheet and having compressed regions throughout at least a substantial part of the second pad. Such a pad is functionally superior to a conventional single pad-type disposable product.

In U.S. Pat. No. 3,612,055 there is disclosed a single pad diaper construction wherein the one surface not in contact with the top sheet is processed to form a paper-like skin to effect fluid spread to the back side of the diaper.

SUMMARY OF THE INVENTION

A principal feature of the present invention is the provision of an absorbent article of simplified construction having both improved fluid dispersing and retention and increased absorption capabilities.

The article of the present invention comprises: a backing sheet of fluid impervious material, a fluid pervious cover sheet and a first absorbent pad adjacent the cover sheet comprising a loosely formed fibrous mass. In a preferred embodiment, either the upper or lower surface of the first pad is coated with an absorbent polymer material for increased absorption capability. This material extends at least a substantial part of the width of the article and extends from the third to the sixth tenth of the length of the pad. The entire pad is not coated because of the high cost of the polymer material and, accordingly, the polycoating is limited to the target area. It has been found that the efficiency of the diaper is greatly increased when the polymer coating is located between the pads. The article has a separate second absorbent pad intermediate the first pad and the backing sheet, with the second pad comprising a mass of fibers having a compressed regions extending throughout a substantial part of the second pad. The average interfiber spacings in the second pad are substantially less than the average interfiber spacings in the first pad.

A feature of the present invention is that the compressed area of the second pad absorbs body fluids from the first pad and rapidly transmits the fluids to other locations of the second pad for feed back to the first pad at the locations of the coatings of abosrbent material.

Antoher feature of the present invention is that the other dispersed fluids are retained in the compressed area of the second pad at a location spaced from the cover sheet.

Thus, a feature of the present invention is that the pads minimize back wetting of the body fluids through the cover sheet and maintain the cover sheet in a relatively dry condition during use of the article.

Yet another feature of the present invention is that the pad may be made in a simplified manner and at a reduced cost.

DESCRIPTION OF THE PREFERRED EMBODIMENTS

Figure 1:
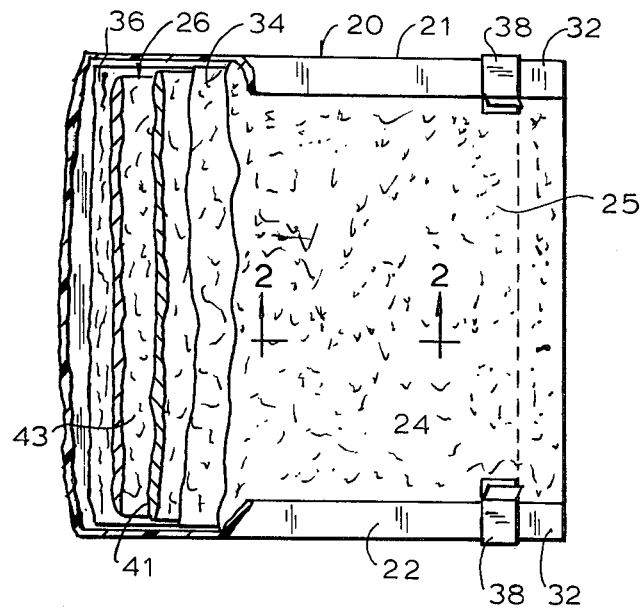
FIG. 1 is a fragmentary front plan view of an absorbent article of the present invention being illustrated in the form of a disposable diaper.
Figure 2:
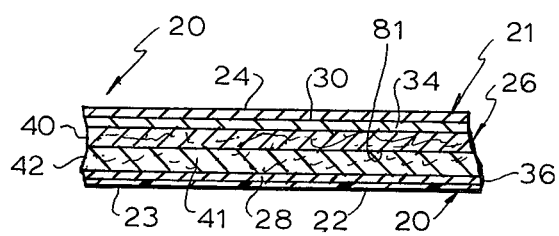
FIG. 2 is a fragmentary sectional view taken substantially as indicated along the plane of line 2—2 in FIG. 1.

Referring now to FIGS. 1 and 2, there is shown a disposable absorbent article generally designated as 20, which is illustrated in the form of a disposable diaper. Although, for convenience, the article of the present invention will be described as a disposable diaper, it will be understood that the principles of the inventions are equally applicable to other disposable absorbent articles, such as sanitary napkins and underpads. As shown, the article or diaper 20 has an abosrbent pad assembly 21 having a fluid impervious backing sheet 22, such as polyethylene, defining a back surface 23 of the pad assembly 21. A fluid pervious top or cover sheet 24, such as of a non-woven material, such as polyethylene or polypropylene fibers or a combination thereof, defines a substantial portion of a front surface 25 of the pad assembly 21. Dual pads generally indicated at 26 are disposed between the cover sheet 24 and the backing sheet 22.

With reference to FIG. 1, the diaper 20 may have a pair of tape fasteners 38 for securing the diaper about an infant during placement and the backing sheet 22 may have lateral side margins 32 folded over and secured to the cover sheet 24 such that the margins 32 cover side portions of the pad assembly 21.

As shown in FIGS. 1 and 2, the absorbent pad assembly 21 has dual pad construction 26 including a first absorbent pad 40 located adjacent the cover sheet 24 and a second absorbent pad 42 located intermediate the first pad 40 and the backing sheet 22. The dual pad construction 26 may optionally have a top wadding sheet 34 covering a front surface 30 of the upper first pad 40 and a back wadding sheet 36 covering a back surface 28 of the lower second pad 42. As shown, a coating 81 of an absorbent material, hereinafter called "polymer," is coated on the back surface of the first pad 40. The absorbent material 81 or polymer coating 81 is selected from one or more of the well-known super-absorbing polymers of the acrylic type, such as the cross-linked poly aerylonitrile and the starch grafted poly acrylonitrile, as well as such products described in U.S. Pat. Nos. 3,645,836, 3,932,322, 4,055,180, 4,055,184, 4,084,591, 4,090,013 and 4,333,461. The coating is preferably disposed between the pads 40 and 42 to substantially increase the efficiency as compared to other coating locations. In addition to coating the back surface 41 of the first pad 40, the polymer coating may be coated on a front surface 43 of the second pad 42.

The first pad 40 is made from a loosely formed mass of fibers, such as comminuted wood pulp, termed in the art as "fluff."

The density of the top pad 40 should be between about 0.03 g/cm$^3$ and about 0.7 g/cm$^3$, preferably between about 0.04 g/cm$^3$ and about 0.07 g/cm$^3$ and more preferably between about 0.06 g/cm$^3$ and about 0.07 g/cm$^3$. The second and lower pad 42 is also made from a mass of fibers, such as comminuted wood pulp, similar to pad 40, but this pad is prepared as by compression or any other suitable conventional means, to a density of between about 0.14 g/cm$^3$ and about 0.22 g/cm$^3$, preferably from about 0.16 g/cm$^3$ and 0.20 g/cm$^3$, and more preferably from about 0.18 g/cm$^3$ and 0.20 g/cm$^3$. Within the aforedescribed parameters of densities, it is desirable that the ratio of the density of the lower pad 42 to that of the top pad 40 be from about 1.5:1 to about 7:1, preferably about 2:1 to 4:1. The densities are, of course, simply determined from a given weight of a measured volume (length×width×thickness with the latter measured as described below).

The thicknesses of the pads may vary widely but, in general, they are combined to give an overall thickness of about 40 mils to 1500 mils (about 1 mm to about 40 mm) with ratios of thicknesses of top to bottom pads ranging from about 50:1 to 1:1, preferably 20:1 to 2:1, and more preferably 10:1 to 4:1. All thicknesses are based upon measurements with a load of 4.1 g/cm$^2$ on the pad since without such an applied load the loftiness and resiliency of the fluff pad would give varying values. Density parameters are then based on such thickness determinations.

For infant diapers total pad thickness will, obviously, be generally lower than for adult incontinuance pads and diapers and for feminine sanitary napkins. Typical newborn infant diapers may have total pad thickness of about 1 mm to about 6 mm or about 2 mm to about 10 mm depending on the diaper style. For larger babies, pad thickness totals may range from about 2 mm to about 8 mm or about 3 mm to about 12 mm. Sanitary napkin pad totals typically may range from about 3 mm to about 10 mm, or about 4 mm to about 20 mm or more, e.g. about 6 mm to about 40 mm, again, depending on the particular style of the sanitary napkin.

Further, it may be desirable to point out that total pad fluff weights will, of course, vary considerably as do the thicknesses and sizes of the pads. As a guide, such weights may vary from about 10 to 20 grams up to about 100 grams. Again, generally, the ratio of the weights of the top to bottom pads may vary from about 2:1 to 1:2 but, preferably, will be about the same, particularly as this permits the greatest facility in manufacture. Thus, for example, a single web of fluff can be formed in any of the conventional ways, then split and the one for the bottom layer compressed as desired in accordance with the present invention.

In use, the diaper 20 is secured about an infant by the tape fasteners 38. During voiding, urine passes through the cover sheet 24 into a localized portion of the first pad 40, and due to the relatively small interfiber spacings in the compressed second pad 42, the fluids are rapidly absorbed from the first pad 40 by the second pad 42. Also, the compressed pad 42 rapidly transmits the fluids to pad portions which are spaced from the point of urine application to the diaper. Although a relatively large amount of fluff material has been compressed in producing the pad 42 and thus it has a smaller fluid holding capacity than the pad 40 due to the relative size of their interfiber spacings, the rapid spreading of the fluid throughout the pad 42 permits the overall pad assembly 26 and polymer coating 81 to retain more fluid as an equivalent weight uncompressed pad assembly much like reservoirs which retain the body fluids in localities but, due to the more rapid and efficient spreading of the urine, there is much less leakage after each urination and also a marked reduction in back wetting, thereby maintaining the top sheet 24 in a relatively dry condition. In this manner, the first and second pads 40 and 42, respectively, cooperate to rapidly disperse fluids throughout the second pad 42 while making maximum use of the pad material and maintaining the top sheet 18 in a relatively dry state.

As previously indicated, the first pad 40 is relatively soft and conformable since it is relatively uncompressed. Accordingly, the first and second pads 40 and 42 respectively provide a pad structure for the diaper which is soft and conformable to the shape of the wearer in order to maximize comfort and provide an excellent fit of the diaper. In addition, the dual pad construction 26 of the present invention may be made in a simplified manner by compressing the second pad 42 and by then placing the first pad 40 against the second pad 42 during manufacture of the diaper. Thus, the diaper is made without the necessity of wetting and drying the compressed regions which would otherwise add to the complexity and cost of manufacture.

Figure 3:
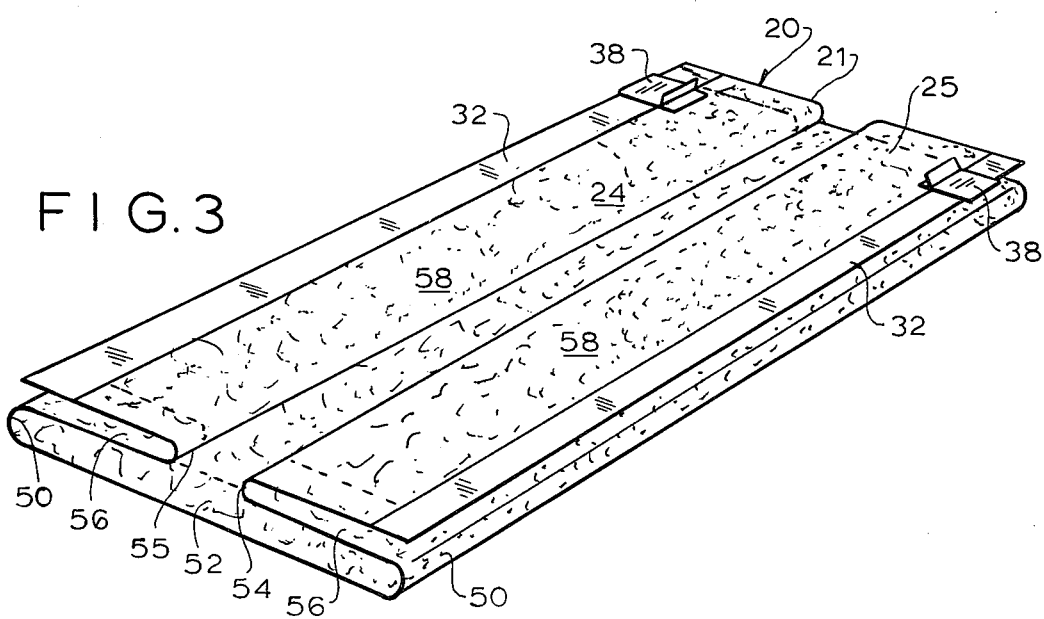
FIG. 3 is a perspective view of the article of FIG. 1 as folded into a box-pleat configuration.

Referring to FIG. 3, the pad assembly 21 of FIG. 1 may be folded along a plurality of longitudinally extending fold lines to define a box-pleat configuration of the diaper. Thus, the diaper is folded along a pair of first fold lines 50 to define a longitudinally-extending central panel 52 and along a pair of second fold lines 54 to define a pair of longitudinally-extending first panels 56 intermediate the fold lines 50 and 54 and a pair of outermost panels 58 extending from the second fold lines 54.

Figure 4:
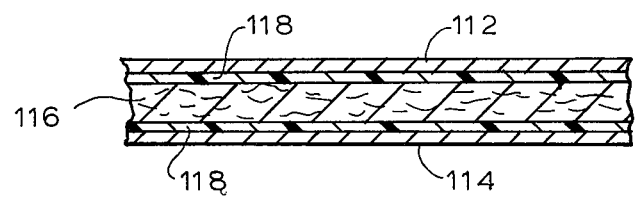
FIG. 4 is a sectional detail view of an alternative form of the invention.
Figure 5:
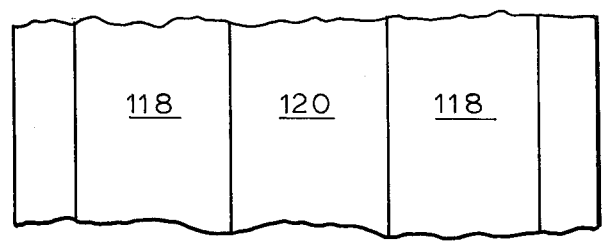
FIG. 5 is a partial plan view of the absorbent pad assembly of the modification of FIG. 4; and, FIG. 6 is a plan view partially broken away for clarity of another form of disposable diaper.

Referring now to the embodiment shown in FIGS. 4 and 5, there is provided a disposable diaper 110, or like absorbent article, which includes a cover sheet 112 of fluid pervious material, a backing sheet 114 of fluid impervious material and an absorbent pad assembly 116 consisting of a single pad of wood fluff or the like. The polymer coating 118 is applied on either surface of the pad 116. If it is applied on the top surface of the pad 116 nearest the cover sheet, a space 120, FIG. 5, is provided between portions of the coating to prevent "gel block." The space 120 between two strips of coating extending the width of the pad and between the third and sixth tenth of the pad was found most efficient in laboratory tests of coatings in the target area. The coatings in the target area are employed in lieu of coatings covering the entire pad because of the high cost of the polymer material used in the coating. The space 120 is provided to eliminate "gel block" at the central point of fluid excretion.

It is to be understood that the coating 81 as applied on the back surface of the pad 40 or the front surface of the pad 42 may likewise be coated in strips. A space between the strips to prevent "gel block" may be provided.

In addition to the preferred forms of the invention wherein the coating 81 is disposed between pads 40 and 42, it is possible to coat alternatively the front surface of pad 40 or the back surface of the pad 42.

Figure 6:
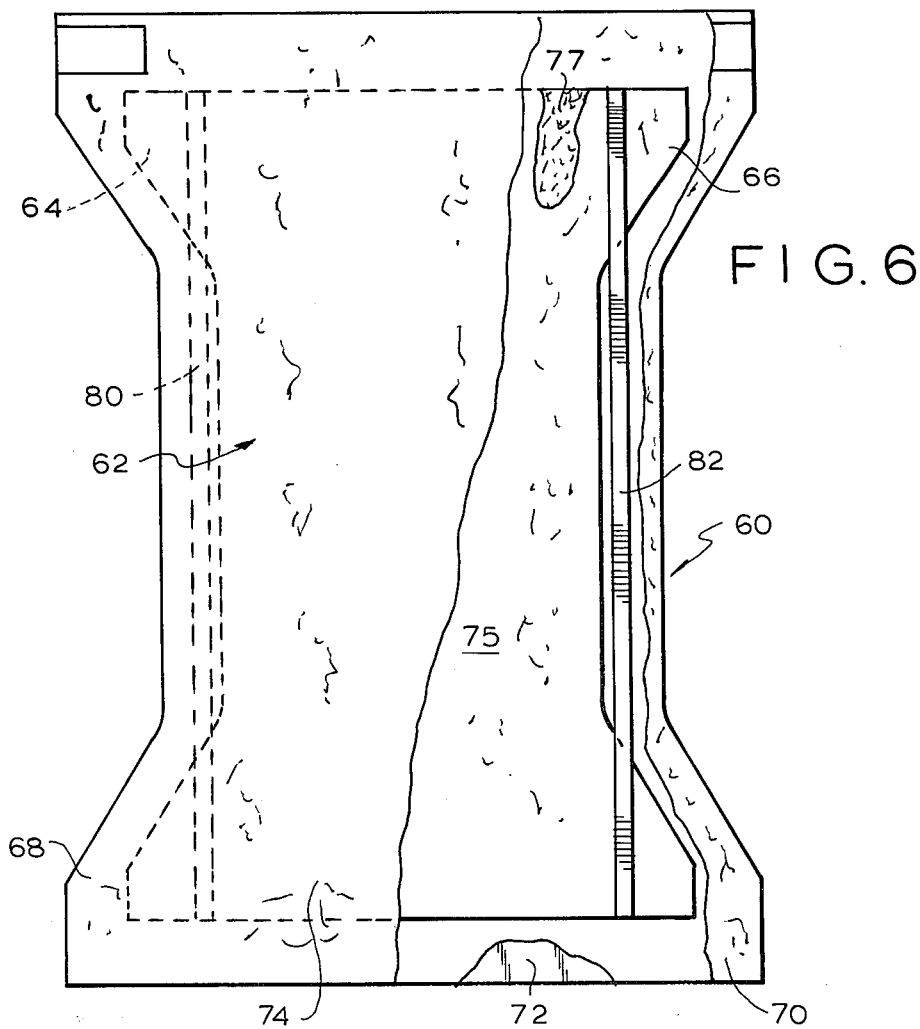

While the embodiment shown in FIG. 3 is a box-pleated configuration, it is possible to employ the invention in a contoured diaper, such as shown in FIG. 6. Herein the diaper 60 is of an hour-glass configuration having a crotch area 62 and four portions of greater width defining ears 64, 66, 68 and 70. The diaper 60 includes a backing sheet 72 of polyethylene or polypropylene film and a top sheet 74 of a non-woven hydrophobic material. An absorbent pad assembly, similar to the dual pad construction 26, is disposed between the top sheet and backing sheets. Waddings 77 may be employed.

A coating of polymer is provided in the crotch area 62 comprising between the third and sixth tenths of the diaper 60. Further, the coating, while preferably applied between the dual pads, may be applied on any surface of either pad. The coating may be applied in bands or strips with a space or spaces therebetween to prevent "gel blockage."

What is claimed is:

1. A disposable diaper comprising a backing sheet of fluid impervious material, a cover sheet of fluid pervious material, an absorbent pad assembly disposed between said backing sheet and said cover sheet, said absorbent pad assembly including a first pad of a loosely formed fibrous mass and a separate second pad of a compressed mass of fibers of less interfiber spacing than the interfiber spacing of said first pad, and a coating of an absorbent polymer material between said first and second pads, said coating extending substantially the full width of said pad assembly, said coating extending from the third to the sixth tenth of the length of the absorbent pad, said coating being in the form of bands having at least one space therebetween to permit fluid flow directly from one pad to the other and freedom from gel blockage.

2. A disposable diaper according to claim 1, wherein said coating is on the surface of said first pad facing away from said cover sheet.

3. A disposable diaper according to claim 1, wherein said coating is on the surface of said second pad facing away from said backing sheet.

* * * * *